United States Patent [19]
Abraham et al.

[11] Patent Number: 6,100,537
[45] Date of Patent: Aug. 8, 2000

[54] MEASURING SYSTEM FOR RECOGNITION OF SURFACE FEATURES

[75] Inventors: Gerhard Abraham, Vienna; Wolfgang Krob, Mödling, both of Austria

[73] Assignee: "MTE" Messgeräte, Entwicklungs- und Vertriebsgesellschaft mbH, Vienna, Austria

[21] Appl. No.: 09/235,047

[22] Filed: Jan. 21, 1999

Related U.S. Application Data

[63] Continuation of application No. PCT/AT97/00171, Jul. 22, 1997.

[51] Int. Cl.⁷ .................................................. G01N 21/86
[52] U.S. Cl. ............................... 250/559.22; 356/239.1
[58] Field of Search .................... 250/559.22, 559.4, 250/559.44, 223 R, 221; 356/239.1, 239.7, 237.2, 376, 430–431

[56] References Cited

U.S. PATENT DOCUMENTS

| 3,835,332 | 9/1974 | Bridges | 250/214 R |
| 5,357,335 | 10/1994 | Sparks | 356/430 |
| 5,557,403 | 9/1996 | Task | 356/239.7 |

FOREIGN PATENT DOCUMENTS

| 0 681 183 | 11/1995 | European Pat. Off. |
| 28 47 935 | 5/1980 | Germany |
| WO 91/10891 | 7/1991 | WIPO |

OTHER PUBLICATIONS

B. Kleinemeier et al: "Halbleitersensoren für die Bilderfassung in der Materialbahninspektion"; Technisches Messen TM, 1982–1988, vol. 54, No. 4, 1987 Munich, Germany, pp. 146–154, XP002046144 (Month unknown).

*Primary Examiner*—Que T. Le
*Attorney, Agent, or Firm*—Henry M. Feiereisen

[57] ABSTRACT

A measuring system for recognition of surface features of a product, (3) e.g. flat glass, rapidly moved on a conveyor (2), with a sensor system (1) that is stationary relative to the moving product (3) and is directed towards the reflecting and/or scattering surface, includes a plurality of transmitter-detector pairs (6, 7) extending transversely to the transport direction (10) of the product (3) and vertically offset to the conveyor (2) along a line, wherein each detector output is connected to an apparatus for determining the intensity of the detector signal, so that the intensity signals of all detectors (7) can be fed in parallel to an evaluation unit (5).

7 Claims, 3 Drawing Sheets

DETECTOR

MEASURING SYSTEM FOR RECOGNITION OF SURFACE FEATURES

CROSS-REFERENCES TO RELATED APPLICATIONS

This application is a continuation of prior filed copending PCT International application no. PCT/AT97/00171, filed Jul. 22, 1997, and claiming the priority of Austrian Patent Application, Ser. No. GM 427/96, filed Jul. 23, 1996, the subject matter of which is incorporated herein by reference.

BACKGROUND OF THE INVENTION

The invention relates, in general, to a measuring system for recognition of surface features of a product, e.g. flat glass, rapidly moved on a conveyor and having a surface which at least partially reflects and/or scatters light, and in particular to a measuring system of a type including a sensor system comprised of a plurality of transmitter/detector elements, preferably of infrared-LED and photodiodes and phototransistors, and directed towards the reflecting and/or scattering surface and stationery relative to the moving product, wherein the light radiating from a transmitter and reflected and/or scattered is received by the associated detector or by the neighboring detectors and converted into an electric signal, and wherein the plurality of transmitter/detector elements is arranged along at least one line extending transversely to the conveying direction of the product and vertically offset to the conveyor.

Many industrial processes which carry out the treatment of rapidly moving product aspire a differentiation between the individually moved pieces which oftentimes area arranged side-by-side on the conveyor.

This is achieved heretofore by several different solutions. It was possible through determination of the dimensions of the product to realize a satisfactory identification. CCD line cameras utilized for this purpose can, however, receive only a limited solid angle. In addition, optical distortions which adversely affect the accuracy of measurement are encountered. In conjunction with flat glass plates, this process has proven inappropriate as the dimensions, such as length and width, cannot be determined with sufficient measuring accuracy. Optical light barriers for dimensional determination have again the significant drawback that different surface conditions of the flat glass yield varying results as a consequence of scattered light.

A further proposal to enable an identification of rapidly moving product views the surface condition as differentiating feature as the product can be easily differentiated thereby.

Especially many applications and fields of operation exist in the glass producing industry because frequently a determination of the surface features must be undertaken, without encountering a shutdown of the manufacturing process.

German Pat. No. DE-A1-28 47 935 discloses an apparatus for automatically detecting defects, contamination or the like of transparent materials such as flat glass, including an optical transmitter arranged transversely to the transport direction of the specimen, and a respective receiver which is movable in transverse direction at parallel distance to the specimen and occupying thereby either a transmission position or a reflection position with respect to the transmitter. The optical receiver is composed of a row of measuring cells and moves during advance of the specimen, with the number of measuring cells depending on the rate of feed. A scanning of the surface is executed to determine even slightest imperfections or contamination.

The optical transmitter is provided in the form of a constant radiation source which is uniformly effective across the entire width of a flat glass pane and examines by light the flat glass pane passing by. Located on the other side is the optical receiver which is composed of several measuring cells and movable at very high speed transversely to the transport direction of the flat glass pane. If an imperfection is encountered during the movement of the receiver, a different measuring value is received. This deviation is converted into an electrical signal to thereby illuminate a signal lamp.

In particular for identification of flat glass plates cut to size according to customer specifications, in addition to other parameters the recognition of surface features is required which the flat glass plates exhibit after the various manufacturing processes.

If the flat glass plates should be subjected, for example, to a tempering process, the flat glass plates must be guided through the tempering oven after being cut to size and possibly treated with a surface coating. As a consequence of the high process temperature, the glass plates cannot be labeled. As the capacity of the tempering oven should be exploited to a highest possible degree, several plates of different shape are typically transported simultaneously through the tempering oven.

After exiting the oven, the plates can be identified with respect to their surface features and associated to respective order data. As the outer shape of the plates of a toughened batch oftentimes differs only slightly, the probability of error during an identification through determination of the dimensions after discharge is relatively high. Therefore, attempts were made to detect a further differentiating criterion in addition to the surface features.

Considered as surface features can be coatings, surface textures, markings, e.g. bar codes etc. In view of the high velocities by which the product is sometimes moved, recognition of surface features can be done by conventional means only in a very difficult manner. In addition, it may be necessary to recognize surface imperfections, e.g. chips, which occur primarily in the area of the edges.

In this context, U.S. Pat. No. 3,835,332 discloses an apparatus for detection of production errors in a web, e.g. a film track. A bar arranged transversely to the direction of movement of an endless film track is equipped with light-emitting diodes in side-by-side disposition for radiating pulsing light which is received by opposing photosensors and converted into a digital code which represents the intensity of the detected light. The detector can thereby be arranged either in transmission position or in reflection position. In this manner, a photographic film can be examined for defects or inaccuracies of the film thickness. The light-emitting diodes are illuminated in sequentially continuously repeating sequence for short intervals, and the reflected light or light transmitted through the track is detected and stored. The recorded data are compared with reference values obtained during a calibration mode of operation in order to detect defects in the web or in the web coating.

The sequential, pulsing control of the light-emitting diodes results in a scanning across the bar arranged transversely to the direction of movement, with the sensors associated to the light-emitting diodes receiving the reflected light pulses or light pulses transmitted through the web for conversion into electric signals. These signals are associated sequentially by an analog-digital-converter in dependence on the intensity to a code which is further processed digitally.

SUMMARY OF THE INVENTION

It is therefore an object of the invention to provide a measuring system of the above-stated type by which a recognition of surface features can be realized even at very high conveying speed.

It is a further object to effect a high-resolution and recognition speed of the surface features.

It is still a further object of the invention to enable a simultaneous recognition of surface features of plates situated side-by-side in transport direction.

This is attained in accordance with the invention by connecting each detector output with an apparatus for determining the intensity of the detectors signal so that the intensity signals of all detectors received during simultaneous radiation of all transmitter-elements can be fed in parallel and simultaneously to an evaluation unit.

The parallel evaluation of the intensities of light reflected and/or scattered from the product surface enables to draw conclusions with respect to the surface features, thereby rendering a simpler identification and association of the product even at very high speeds possible. In this manner, e.g. surface coatings and surface textures as well as defects such as edge chips can be detected at high accuracy.

According to a further development of the invention, respectively neighboring transmitter/detector elements are arranged at slight distance, preferably in abutting disposition, thereby increasing the resolution of the measurement and thus the reproducibility of the measuring results.

According to a particularly preferred feature of the invention, the linear sensor system extends across the entire width of the conveyor. In this manner, all workpieces moveable by the conveyor can be detected.

According to a further variation of the invention, the linear sensor system is vertically adjustable by an apparatus for height adjustment.

In this manner, the measuring system according to the invention can be so suited to the respectively moved product that the detectors can receive a maximum intensity of the reflected and/or scattered light. Normally, the height is so adjusted as to insure a constant distance to the product surface.

According to a further variation of the invention, the plurality of transmitter/detector elements can be arranged along two parallel, spaced-apart lines, whereby for each transmitter/detector element of the one line a corresponding transmitter/detector element of the other line is provided.

Through such an arrangement, the surface features can be detected sequentially twice, thereby allowing an averaging of the measuring values so that the measuring security is increased, on the one hand, and a use for a measurement of velocity of the moving product. It may, however, also be suitable to use a different number of transmitter/detector elements in both lines.

In accordance with a further object of the invention, a process for recognition of surface features of a product rapidly moved by a conveyor and exhibiting a surface at least partially reflecting and/or scattering light is proposed, which process measures the intensities of a plurality of light rays reflected and/or scattered from the surface of the product along at least one line extending transversely to the transport direction of the product, and which process is able to realize a high measuring security and accuracy.

This is attained in accordance with the invention by simultaneously radiating the plurality of light rays, by simultaneously measuring the intensities of the reflected and/or scattered light rays, and by determining the surface features of the moving product from the pattern of the reflected and/or scattered intensities along the line extending transversely to the transport direction.

In this manner, the surface features can be precisely determined even for products that are moved very rapidly, and used for identification.

In accordance with a further development of the invention, the intensities are measured along two parallel, spaced-apart lines, and the measuring values of equivalent transmitter/detector elements are compared to one another, and based on their sequence in time the velocity of the moving product is determined.

The determination of the measuring value can be improved in this manner, and the velocity of the product can be determined through detection of two identical textures, coatings, surface imperfections or the like, so that precise conclusions can be drawn about the length dimensions of the product respectively passing by.

BRIEF DESCRIPTION OF THE DRAWING

The above and other objects, features and advantages of the present invention will no be described in more detail with reference to the accompanying drawing, in which.

DETAILED DESCRIPTION OF PREFERRED EMBODIMENTS

Figure 1:
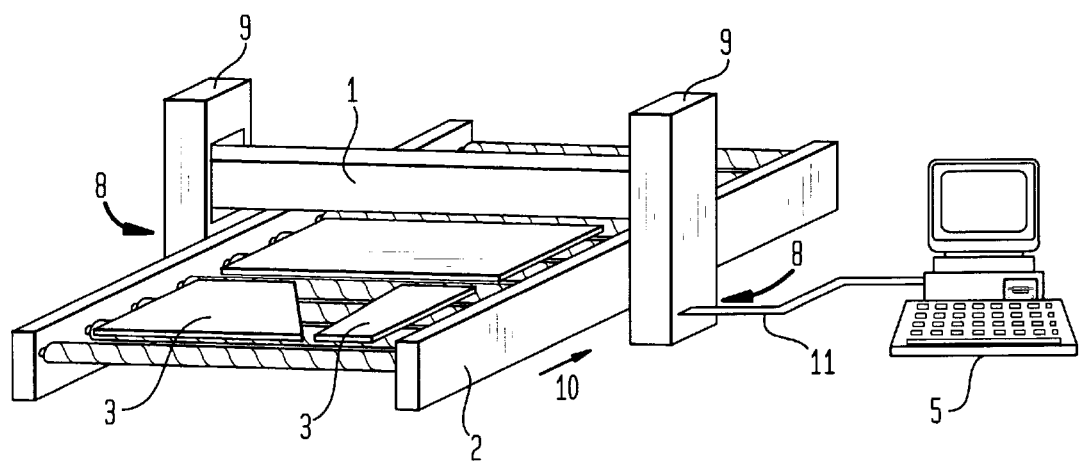
FIG. 1 is a perspective side view of one embodiment of the measuring system according to the invention.
Figure 2:
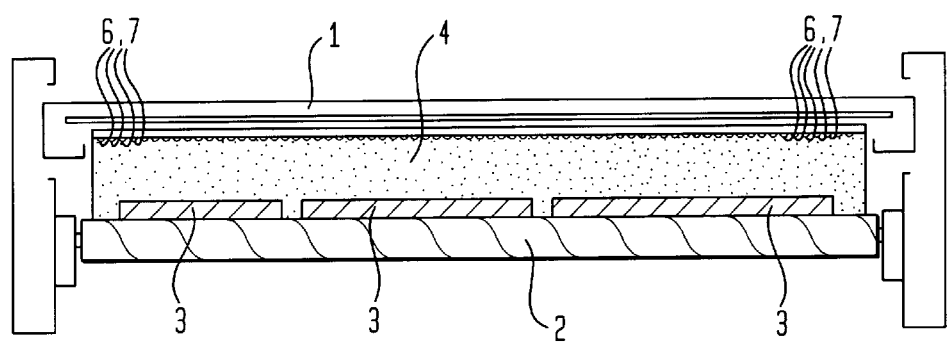
FIG. 2 is a section transversely to the transport direction of the conveyor of one embodiment of the measuring system according to the invention.

Throughout all the Figures, same or corresponding elements are generally indicated by same reference numerals.

FIG. 1 shows the overall view of a measuring system which enables the contactless measurement of surface features of a product moved rapidly on a conveyor 2. In this exemplified embodiment, the conveyed product is flat glass which has a surface at least partially reflecting and/or scattering light and moved by a conveyor in the form of a roller-type conveyor 2 from one stage of the manufacturing process to the next stage. Also any other reflecting and/or scattering material may be useable as product.

Figure 3:
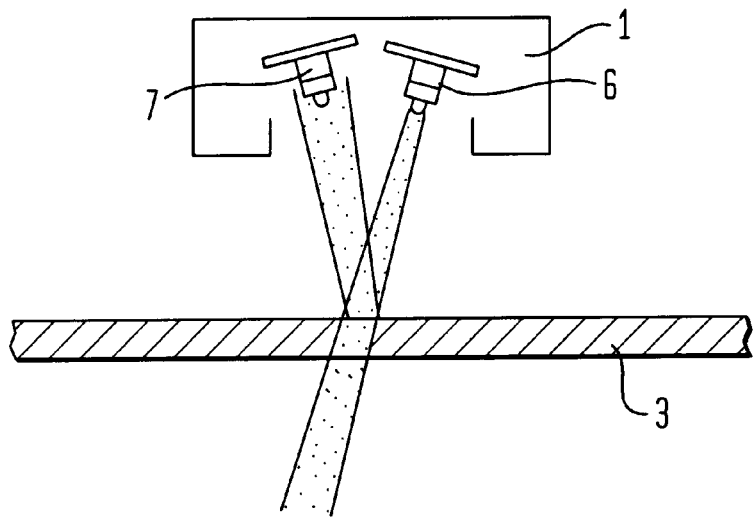
FIG. 3 is a longitudinal section through the sensor system of one embodiment of the measuring system according to the invention.

Directed toward the reflecting and/or scattering surface of the rapidly moved product 3 is, in accordance with the invention, a sensor system 1 which is stationary relative to the moving product 3 and comprised of a plurality of pairs of transmitter/detector elements 6, 7, preferably infrared-LED and photodiodes and phototransmitters, with light radiating from each transmitter 6 and reflected and/or scattered from the product surface being received in the associated detector 7 and/or neighboring detectors 7, for conversion into a respective electric signal (FIG. 3).

In this context, it should be noted that the invention is by no means limited to the described types of transmitters and detectors, rather all respectively appropriate ones, e.g. laser diodes, for all wavelength ranges should be covered.

The plurality of transmitter/detector elements 6, 7 is arranged transversely to the transport direction 10 of the product 3 and vertically offset to the conveyor plane of the roller-type conveyor 2 along a line. It is however also possible to provide the measuring system according to the invention with several of these linear arrangements. Each detector output is connected with a (not shown) apparatus for determining the intensity of the detector signal, e.g. an analog/digital converter, so that the intensity signals of all detectors 7 can be fed in parallel via a measuring line 11 to an evaluation unit 5, e.g. a PC. The transmitters 6 and the detectors 7 are accommodated in a bridge 1 which is arranged above the drums 3 of the roller-type conveyor and supported by columns 8 on both sides, with the bridge generating a light curtain 4 as a consequence of its tight arrangement.

An exemplified realization for a conveyor of 2.5 m width, which by no means limits the invention, includes 70 microprocessors, each having 32 parallel A/D inputs for processing measuring values, for supply of the data in parallel to the evaluation unit 5.

In this context, it should be emphasized that unlike the prior art no sequential scanning of the individual detector outputs is carried out, but the signals of all detectors 7 are received simultaneously for each measurement.

The measuring system according to the invention allows execution of the process according to the invention which includes a simultaneous measurement of the intensities of a plurality of light rays reflected and/or scattered from the surface along a line extending transversely to the transport direction, and a determination of the surface features of the moving product 3 on the basis of the pattern of the reflected and/or scattered intensities along the line extending transversely to the transport direction.

Figure 4:
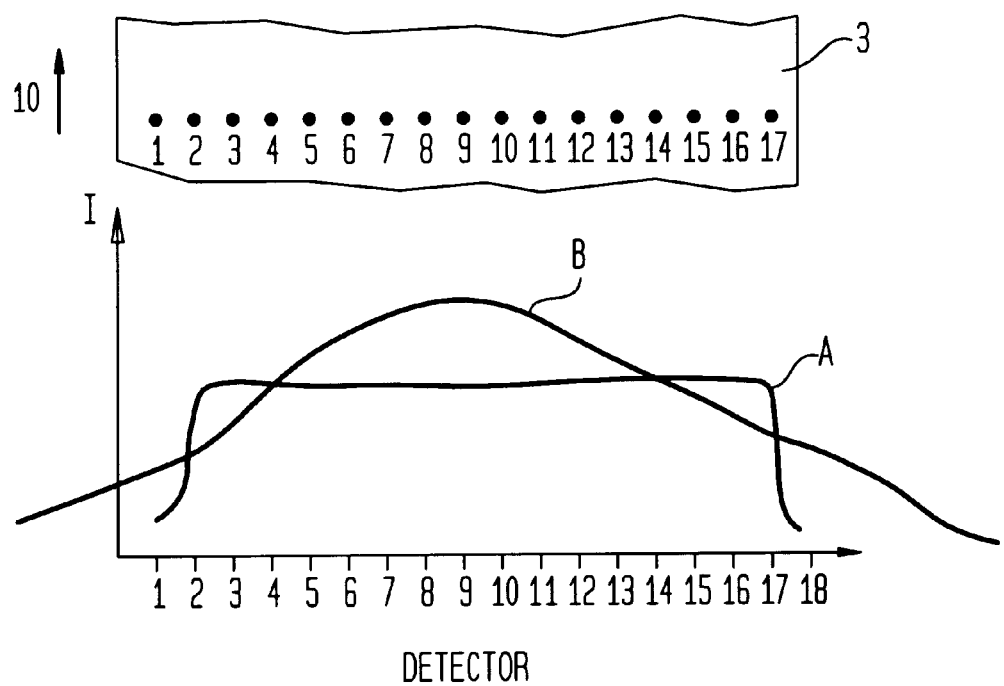
FIG. 4 is a schematic illustration and a diagram of the intensity pattern of two different surface conditions along the line of light points.

FIG. 4 shows a schematic illustration in which, by way of example, impact points 1 to 18 generated on the moving product surface by eighteen light rays arranged along a line are illustrated, from which the reflected and/or scattered rays reach the detectors. By parallel evaluation of measurement of the intensities, i.e. by simultaneous determination of all eighteen reflected and/or scattered intensities, which in part may be generated also through superposition of light rays scattered in different angles, their dependency along this line, as shown in FIG. 4, can be reproduced, whereby from the pattern conclusions can be drawn with respect to the surface features, with pattern A relating e.g. to smooth flat glass allowing a good reflection, and curve B relating to randomly scattering rough flat glass. Thus, differently treated flat glasses can be effectively differentiated from one another during the transport from one plant to the next one, without requiring a manual examination. In addition, the determination of the measuring value does not require a reduction of the conveying speed so that no slow-down or back-up of product being conveyed can be experienced.

Curve B also shows the reason why solutions using light barriers for determination of the dimensions of flat glasses are only suitable to a limited degree. As a consequence of the scattering, the optically determined curve of the moving product is blurred so that no reliable YES/NO assertion is possible with respect to the intensity and thus about the dimensions. The evaluation of the detector signals, in accordance with the invention, enables besides the recognition of surface features in addition a more precise determination of the dimensions of the product in comparison with processes known to date.

In order to realize a best possible resolution, respectively neighboring transmitter/detector elements 6, 7 are spaced at slight distance from one another, preferably in abutting disposition.

Thus, when using currently commercially available transmitters 6 and detectors 7 at respective space-saving arrangement, a resolution of the intensity measurement of up to 1 mm may be accomplished, whereby for typical dimensions the transmitter/detector pairs grow to a relatively great number. A size reduction of the transmitters and detectors leads, by nature, to an increase of the resolution.

Moreover, the linear sensor system 1 includes an apparatus for height adjustment 9 by which the sensor system is vertically adjustable. In this manner, the bridge 1 with the plurality of transmitters 6 and detectors 7 can be vertically adjusted via a respective balancing device until approximately a relative maximum of the detector output signal or continuously a predetermined distance to the product surface is adjusted.

Figure 5:
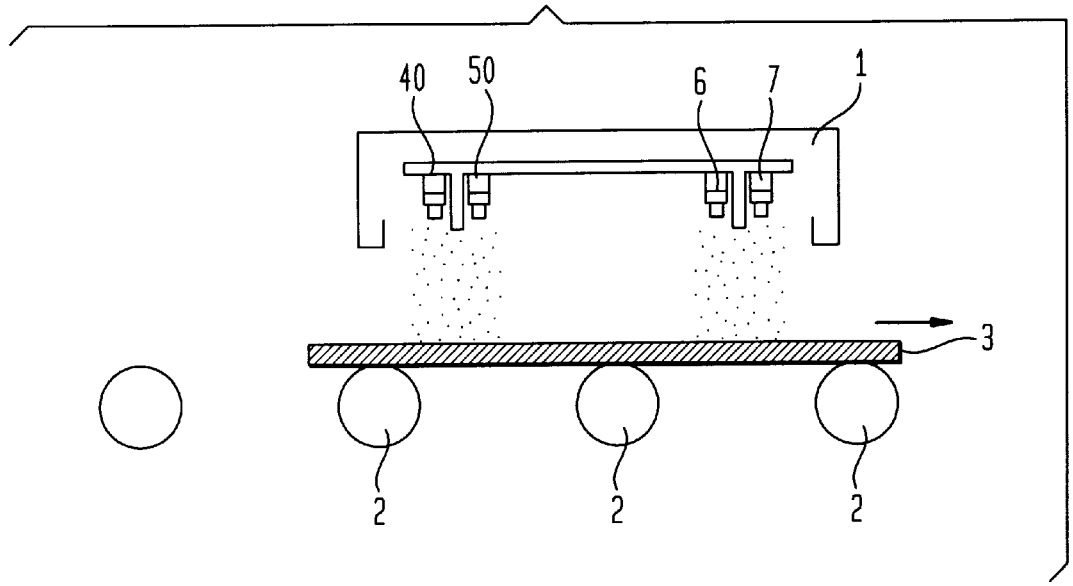
FIG. 5 is a longitudinal section through the sensor system of a further embodiment of the measuring system according to the invention.

FIG. 5 shows a further variation according to the invention, in which a plurality of transmitter/detector elements 6, 7; 40, 50 are arranged along two parallel, spaced-apart lines, whereby for each transmitter/detector element 6, 7 of the one line a respective transmitter/detector element 40, 50 of the other line is provided. A surface feature determined by the detector 50 of the first line is thus registered by the respective detector 7 of the second line by a time delay which is dependent on the conveying speed. Serving as feature may be the coating, the texture, e.g. an ornament, realized by a preceding process, but also imperfections, edge chips encountered during cutting or breaking of the flat glass plate, or a bar code with widely spaced single bars in correspondence with the resolution.

The intensities along the two parallel, spaced-apart lines are measured, and the measuring values of equivalent transmitter/detector elements 6, 7; 40, 50 are compared to one another, and the speed of the moving product is determined on the basis of their timed sequence.

While the invention has been illustrated and described as embodied in a measuring system for recognition of surface features, it is not intended to be limited to the details shown since various modifications and structural changes may be made without departing in any way from the spirit of the present invention.

What is claimed as new and desired to be protected by Letters Patent is set forth in the appended claims:

1. A measuring system for recognition of surface features of a product, (3) e.g. flat glass, rapidly moved on a conveyor (2) and having a surface which at least partially reflects and/or scatters light, with a sensor system (1) comprised of a plurality of transmitter/detector elements (6, 7), preferably of infrared-LED and photodiodes and phototransistors, being provided which is directed towards the reflecting and/or scattering surface of the product and stationary relative to the moving product (3), wherein the light radiating from each transmitter element (6) and reflected and/or scattered is received by the associated detector element (7) and/or by the neighboring detector elements (7) and converted into an electric signal, and wherein the plurality of transmitter/detector elements (6, 7) is arranged along at least one line extending transversely to the transport direction (10) of the product (3) and vertically offset to the conveyor, wherein each detector output is connected to an apparatus for determining the intensity of the detector signal, so that the intensity signals of all detector elements (7), received upon simultaneous radiation of all transmitter elements (6), are fed in parallel and simultaneously to an evaluation unit (5).

2. The measuring system of claim 1 wherein transmitter/detector elements (6, 7) are arranged at slight distance to one another, preferably in abutting disposition.

3. The measuring system of claim 1 wherein the sensor system is a linear sensor system which extends across the entire width of the conveyor (2).

4. The measuring system of claim 1 wherein the sensor system is a linear sensor system (1) which is vertically adjustable by an apparatus for height adjustment.

5. The measuring system of claim 1 wherein the plurality of transmitter/detector elements (6, 7; 40, 50) is arranged along two parallel, spaced-apart lines, whereby for each transmitter/detector element (6, 7) of the one line, there is provided a respective transmitter/detector element (40, 50) of the other line.

6. A process for recognition of surface features of a product (3) rapidly moved by a conveyor and exhibiting a surface at least partially reflecting and/or scattering light, whereby the intensities are measured of a plurality of light rays reflected and/or scattered from the surface of the product (3) along at least one line extending transversely to the transport direction (10) of the product (3), wherein the plurality of light rays are emitted simultaneously, that the intensities of the reflected and/or scattered light rays are measured simultaneously, and that the surface features of the moved product (3) are determined on the basis of the pattern of the reflected and/or scattered intensities along the line extending transversely to the transport direction (10).

7. The process of claim 6 wherein the intensities along two parallel, spaced-apart lines are measured, and the measuring values of equivalent transmitter/detector elements (6, 7, 40, 50) are compared to one another, and based on the timed sequence the speed of the moving product (3) is determined.

* * * * *